(12) United States Patent
Chang

(10) Patent No.: US 6,261,794 B1
(45) Date of Patent: Jul. 17, 2001

(54) METHODS FOR IDENTIFYING INHIBITORS OF METHIONINE AMINOPEPTIDASES

(75) Inventor: Yie-Hwa Chang, St Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 09/418,135

(22) Filed: Oct. 14, 1999

(51) Int. Cl.[7] .................................................. C12Q 1/37
(52) U.S. Cl. ............................................... 435/23; 435/24
(58) Field of Search .................................. 435/23, 6, 24, 435/69.1, 69.4; 514/12, 15, 44; 530/350

(56) References Cited

U.S. PATENT DOCUMENTS

| | | | |
|---|---|---|---|
| 4,119,620 | * 10/1978 | Nagatsu et al. | ............... 260/112.5 R |
| 5,885,820 | 3/1999 | Chang . | |
| 6,136,604 | * 10/2000 | Monia et al. | ........................ 435/375 |

OTHER PUBLICATIONS

Lin, Y. Purification and Characterization of an Enzyme Hydrolyzing L–Methionine–4–Nitroanilide From Germinated Sweet Potato Roots. Bot Bull Acad Sin 35:25–32, 1994.*

Klinkenberg M. A Dominant Negative Mutation in *Saccharomyces cerevisiae* Methionine Aminopeptidase–1 Affects Catalysis and Interferes with the Function of Methionine Aminopeptidase–2. Archives of Biochemistry and Biophysics 347(2)193–200, Nov. 1997.*

Chang Y. Purification and Characterization of a Methionine Aminopeptidase from *Saccharomyces cerevisiae*. J of Biological Chemistry 265(32)19892–19897, Nov. 1990.*

Aoyagi et al.Release of a Plasma Membrane–Bound Triaminopeptidase Activity from mammalian Cells by Thermolysin, *Biochem, Biophys. Res. Commun.* 80:435 (1978).

Ben–Bassat et al., Processing of the Initiatoin Methionine from Proteins: Properties of the *Escherichia coli* Methionine Aminopeptidase and Its Gene Structure, *J. Bacteriol.* 169:751–757 (1987).

Bradshaw et al., N–Terminal processing: the methionine aminopeptidase and $N^{60}$–acetyl transferase families, *Trends Biochem. Sci.* 23:263–267 (1998).

Carter et al., Aspartate–Specific Peptidase in *Slammonella typhimurium*: Mutants Deficient in Peptidase E, *J. Bacteriol.* 159:453–459 (1984).

Cohen et al., Amino Acid Analysis Utilizing Phenylisothiocyanate Derivatives, *Anal. Biochem.* 174:1–16 (1988).

Doi et al., Modified Colorimetric Ninhydrin Methods for Peptidase Assay, *Anal. Biochem.* 118:173–184 (1981).

Doughty and Gruenstein, Chloride –insensitive, glycine–phenylalanine–naphthylamide hydrolysis at neurtral pH in human skin fibroblasts, *Biochem. and Cell Biol.* 64:722 (1986).

Ikehara et al., Dipeptidyl–peptidase IV from Rat Liver, *Meth. Enzymol.* 244:215–227 (1994).

Jadot et al., Intralysosomal hydrolysis of glycyl–L–phenylalanine 2–naphthylamied, *Biochem. J.* 219:965 (1984).

Larrabee et al., High–Pressure Liquid Chromatopgraphic Method for the Assay of Methionine Aminopeptidase Activity: Application to the Study of Enzymatic Inactivation, *Anal. Biochem,* 269:194–198 (1999).

Liu et al., Structure of Human Methionine Aminopeptidase–2 Complexed with Fumagilin, *Science* 282:1324–1327 (1998).

Lowther et al., The anti–angiogenic agent fumagillin covalently modifies a conserved active–site histidine in the *Escherichia coli* methionine aminopeptidase, *Proc. Natl. Acad. Sci. USA* 95:12153–12157 (1998).

Moerschell et al., The Specificities of Yeast Methionine Aminopeptidase and Acetylation of Amino–terminal Methionine in Vivo, *J. Biol. Chem.* 265:19638–19643 (1990).

Moore et al., Chromatography of Amino Acids on Sulfonated Polystyrene Resins, *Anal. Biochem.* 30:1185–1190 (1958).

Proost et al., Truncation of Macrophage–derived Chemokine by CD26/Dipeptidyl–Peptidase IV beyond its Predicted Cleavage Site Affects Chemotactic Activity and CC Chemokine Receptor 4 Interaction, *J. Biol. Chem.* 274:3988–3993 (1999).

Roth, Fluorescence Reaction for Amino Acids, *Anal. Chem.* 43:880–882 (1971).

Stein et al., Amino Acid Analysis with Fluorescamine at the Picomole Level, *Arch. Biochem. Biophys.* 155:202–212 (1973).

Tsunasawa et al., Amino–terminal Processing of Mutant Forms of Yeast Iso–1–cytochrome c, *J. Biol. Chem.* 260:5382–5391 (1985).

Walker et al., Yeast (*Saccharomyces cerevisiae*) methionine aminopeptidase I: rapid purification and improved activity assay, *Biotechnol Appl. Biochem.* 29:157–163 (1999).

Zuo et al., A Protease Assay via Precolumn Derivatization and Hihg–Performance Liquid Chromatography, *Anal. Biochem.* 222:514–516 (1994).

* cited by examiner

*Primary Examiner*—Ralph Gitomer
(74) *Attorney, Agent, or Firm*—Howell & Haferkamp, L.C.

(57) ABSTRACT

Methods are provided for detecting methionine aminopeptidase (MAP) activity and for detecting inhibitors of MAP. The methods utilize a peptide comprising an N-terminal methionine which can be cleaved from the peptide by MAP, and a C-terminal detection moiety which is released by a second peptidase only if the N-terminal methionine has been cleaved from the peptide. When the peptide is combined with MAP and the second peptidase, the detection moiety is released, while the addition of a MAP inhibitor will inhibit the release of the detection moiety. Reaction mixes, peptides, and kits which are useful for practicing the methods are also provided.

13 Claims, 3 Drawing Sheets

A. Met-Gly-Pro-pNA → Met + Gly-Pro-pNA

B. Gly-Pro-pNA → Gly-Pro + pNA

Figure 1

METHODS FOR IDENTIFYING INHIBITORS OF METHIONINE AMINOPEPTIDASES

This invention was made with Government support under National Science Foundation Grant No. MCB 9512655. The Government has certain rights in the invention.

BACKGROUND OF THE INVENTION (1) Field of the Invention

The present invention generally relates to assays for enzyme activity and for enzyme inhibitors. More specifically, the invention relates to assays for detecting methionine aminopeptidases and inhibitors of methionine aminopeptidases.

(2) Description of the Related Art

In all living cells, protein synthesis is initiated with an AUG codon, specifying methionine as the N-terminal amino acid in nascent proteins. In both prokaryotes and eukaryotes, this N-terminal methionine will be removed by a methionine aminopeptidase (MAP) (EC 3.4.11.18) if the penultimate amino acid residue is small and uncharged, e.g., Gly, Ala, Ser, Cys, Thr, Pro, and Val, although methionine cleavage activity by MAP is reduced when the N-terminal three amino acids are Met-Thr-Pro or Met-Val-Pro (Moerschell et al., 1990, *J. Biol. Chem.* 265, 19638–19643; Tsunasawa et al., 1985, *J. Biol. Chem.* 260, 5382–5391). Removal of the N-terminal methionine is essential for certain proteins to function normally in vivo. For example, the removal of the initiator methionine is often required for subsequent N-terminal modifications, such as N-myristoylation, which is essential for the normal function of various signal transduction proteins, cancer cells, protein targeting moieties, and enzymes (Gordon et al., 1991, *J. Biol. Chem.* 266, 8647–8650; Duronio et al., 1989, *Science* 243, 796–800).

Methionine aminopeptidases have been isolated and cloned from several organisms, including *E. coli* and several other eubacteria, yeast, rat, and various archaea. Currently discovered MAPs have been categorized into two types, type 1 MAP and type 2 MAP, based on structural and sequence similarities. Eubacteria have type 1, archaea have type 2, and eukaryotes have both types. In eukaryotes, null mutants in either type are viable but slow growing, but null mutants of both MAP types are nonviable (Li and Chang, 1995, *Proc. Natl. Acad. Sci. USA* 92, 12357–12361; Li and Chang, 1996, *Biochem. Biophys. Res. Commun.* 227, 152–159; Bradshaw et al., 1998, *Trends Biochem. Sci.* 21, 285–286). Similarly, knockouts of the bacterial MAP1 gene are lethal (Ben-Bassat et al., 1987, *H. Bacteriol.* 169, 751–757). Thus, MAP activity is essential for normal functioning of prokaryotic and eukaryotic cells.

Aside from their role in cleaving the initiator methionine of proteins, MAPs affect other cellular functions. For example, human type 2 MAP also serves as eukaryotic initiation factor-2, which regulates protein synthesis (U.S. Pat. No. 5,885,820). Also, the mode of action of fumagillin-type angiogenesis inhibitors is the irreversible inhibition of type 2 MAP (Griffith et al., 1997, *Chem. Biol.* 4, 461–471; Liu et al., 1998, *Science* 282, 1324–1327; Lowther et al., *Proc. Natl. Acad. Sci. USA* 95, 12153–12157; Sin et al., 1997, *Proc. Natl. Acad. Sci. USA* 94, 6099–6103) thus indicating an essential role of type 2 MAP in angiogenesis.

Because of the crucial role of MAPs in prokaryotic and eukaryotic functions, there is an interest in the discovery of additional inhibitors of these enzymes, which may serve as antibiotics or as chemotheraputic agents which inhibit angiogenesis in tumors. However, current methods for monitoring MAP activity are inadequate for this task. These methods include the colorimetric ninhydrin method (Doi et al., 1981, *Anal. Biochem.* 118, 173–184); amino acid oxidase treatment followed by peroxidase reaction and o-dianisidine color development (Carter and Miller, 1984, *J. Bacteriol.* 159, 453–459); amino acid analysis via ion exchange chromatography followed by postcolumn derivatization with ninhydrin (Moore et al., 1958, *Anal. Biochem.* 30, 1185–1190), fluorescamine (Stein et al., 1973, *Arch. Biochem. Biophys.* 155, 202–212), or o-phthalaldehyde/β-mermercaptoethanol (Roth, 1971, *Anal. Chem* 43, 880–882); precolumn derivatization of amino acids followed by reverse phase HPLC chromatography (Cohen and Strydom, 1988, *Anal. Biochem.* 174, 1–16; Zuo et al., 1994, *Anal. Biochem.* 222, 514–516); and separation of substrate peptides and products by reverse phase HPLC with on-line UV detection of each separated compound (Larrabee et al., 1999, *Anal. Biochem.* 269, 194–198; Walker et al., 1999, *Biotechnol. Appl. Biochem.* 29, 157–163). These methods are either not sensitive or accurate enough for quantitative assays, or are not rapid enough for high-throughput screening procedures. Thus, there is a need for new assays for MAP activity which are rapid and quantitative enough for use in procedures requiring high-throughput MAP analysis, such as screening for MAP inhibitors.

SUMMARY OF THE INVENTION

Accordingly, the inventor has succeeded in inventing a novel MAP assay which is rapid, quantitative, and suitable for automated procedures. The assay employs a second peptidase and a peptide which comprises an N-terminal methionine which can be cleaved by MAP, along with a C-terminal detection moiety which can be released from the peptide by the second peptidase only if the N-terminal methionine has been cleaved from the peptide.

Thus, one embodiment of the invention is directed to methods for detecting methionine aminopeptidase (MAP) activity in a composition. These methods comprise (a) combining the composition with a peptide comprising an N-terminal methionine under conditions that the N-terminal methionine can be cleaved from the peptide by a MAP to produce a cleaved peptide, wherein the peptide contains a C-terminal detection moiety which is released by a second peptidase only if the N-terminal methionine has been cleaved from the peptide; (b) reacting any cleaved peptide produced in (a) with the second peptidase to release the detection moiety; and (c) detecting any detection moiety released. A preferred second peptidase is dipeptidyl peptidase IV. When dipeptidyl peptidase IV is utilized, a preferred peptide comprises Met-$X_{aa}$-Pro, wherein $X_{aa}$ is Ala, Cys, Gly, or Ser; a most preferred peptide is Met-Gly-Pro-p-nitroanilide.

The present invention is also directed to methods for determining whether a substance inhibits a MAP. The methods comprise (a) combining the substance, the MAP, and a peptide comprising an N-terminal methionine under conditions that the N-terminal methionine can be cleaved from the peptide by the MAP to produce a cleaved peptide, wherein the peptide contains a C-terminal detection moiety which is released by a second peptidase only if the N-terminal methionine has been cleaved from the peptide; (b) reacting any cleaved peptide produced in (a) with the second peptidase to release the detection moiety; and (c) detecting any detection moiety released. As with the previously described method, a preferred second peptidase is dipeptidyl peptidase IV, and a preferred peptide is Met-Gly-Pro-p-nitroanilide.

This method also preferably comprises quantitating the amount of detection moiety released, in order to more accurately detect MAP inhibitors.

In another embodiment, the present invention is directed to reaction mixtures suitable for use in the methods described above. The reaction mixture comprises (a) a peptide comprising an N-terminal methionine which can be cleaved by the methionine aminopeptidase, and a C-terminal detection moiety which can be released by a second peptidase only if the N-terminal methionine has been cleaved from the peptide; and (b) the second peptidase. A MAP may also be included in the mixture.

In an additional embodiment, the present invention is directed to a kit for performing the methods described above, comprising the second peptidase and the peptide described in those methods, along with instructions for performing the methods. Preferably, the kit also comprises a MAP.

The present invention is also directed to the peptides described in the above embodiments.

Among the several advantages achieved by the present invention, therefore, may be noted the provision of methods and reagents for rapidly detecting and quantifying MAP activity and MAP inhibitor activity. These methods are more suitable than previously known methods for rapid screening and quantifying MAP and MAP inhibitor activity because they combine speed, quantitative accuracy, and potential for automated execution, which has not been previously achieved.

BRIEF DESCRIPTION OF THE DRAWINGS

FIG. 1 depicts reactions catalyzed by MAP (A) and dipeptidyl peptidase IV (B) which are useful in the present invention.

DESCRIPTION OF THE PREFERRED EMBODIMENTS

The present invention is directed to rapid and quantitative MAP assays. These assays employ a second peptidase and a peptide, wherein the peptide comprises an N-terminal Met which is capable of being cleaved by MAP, and a C-terminal detection moiety which is capable of being released from the peptide by the second peptidase only if the N-terminal Met has been cleaved from the peptide. The detection moiety is not detectable when it is covalently bound to the peptide but becomes detectable upon its release from the peptide.

It has been known that peptide analogs such as Leu-p-nitroanilide serve as a substrate for aminopeptidases such as leucine aminopeptidase (EC 3.4.11.1). When conjugated to Leu, p-nitroanilide absorbs much less light at 405 nm than when released from the amino acid. Thus, cleavage of Leu-p-nitroanilide by leucine aminopeptidase to form leucine +p-nitroanilide is accompanied by a quantitative increase in $A_{405}$. However, MAP cannot cleave Met-p-nitroanilide to release p-nitroanilide.

It is also known that other enzymes are able to use a short peptide conjugated to p-nitroanilide or other such detection moieties as a substrate, releasing p-nitroanilide. One notable example is dipeptidyl peptidase IV (EC 3.4.14.5)(also known as leukocyte differentiation antigen CD26) which will cleave $X_{aa}$-Pr-p-nitroanilide, where $X_{aa}$ is any amino acid, to release p-nitroanilide (e.g., reaction B in FIG. 1). Dipeptidyl peptidase IV can also utilize Ala and hydroxyproline as the penultimate amino acid (in place of Pro), albeit with slower release of the detection moiety (Ikehara et al., 1994, *Meth. Enzymol.* 244, 215–227). It has also recently been discovered that dipeptidyl peptidase IV can utilize an N-terminal Tyr-Gly as a substrate (Proost et al., 1999, *J. Biol. Chem.* 274, 3988–3993).

Figure 2:
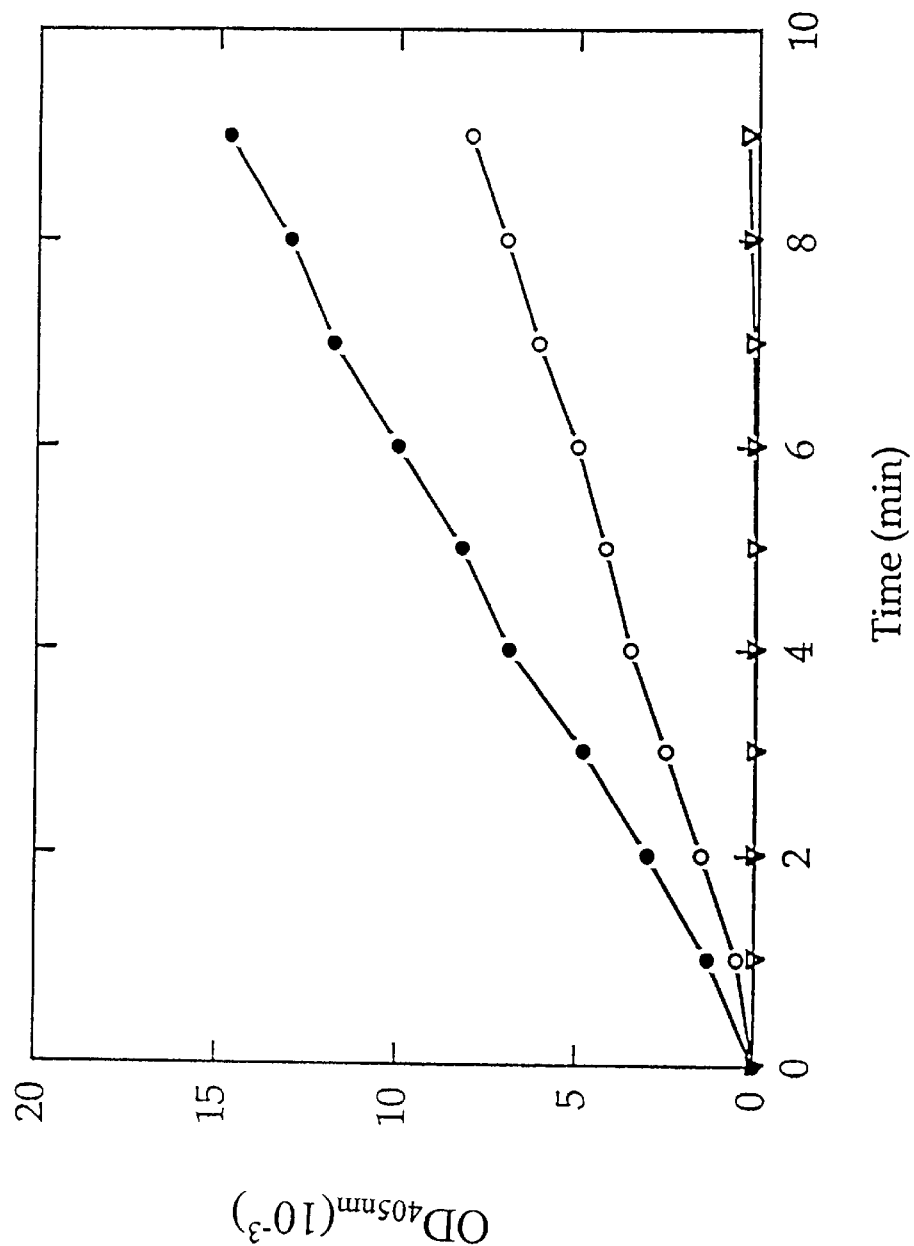
FIG. 2 is a graph depicting the results of an assay for MAP according to the invention, using the peptide Met-Gly-Pro-p-nitroanilide, where dipeptidyl peptidase IV is able to release p-nitroanilide in the presence of type 1 MAP (•—•) and type 2 MAP (o—o), but not with dipeptidyl peptidase IV alone (∇—∇).

It has now been discovered that, when either type 1 or type 2 MAP is mixed with Met-Gly-Pro-p-nitroanilide and dipeptidyl peptidase IV, p-nitroanilide is released from the peptide, whereas no p-nitroanilide is released when MAP is not included (FIG. 2). Thus, MAP is able to utilize a tripeptide as a substrate, mediating, e.g., reaction A in FIG. 1 to create Gly-Pro-p-nitroanilide, which dipeptidyl peptidase IV can use as a substrate to release p-nitroanilide.

As used herein, the term "release", when referring to a detection moiety on a peptide, means that the covalent bond between the detection moiety and the peptide has been broken, generally by enzymatic action.

Thus, in some embodiments of the invention, methods for detecting MAP activity in a composition is provided. These methods comprise combining the composition with a peptide comprising an N-terminal methionine under conditions that the N-terminal methionine can be cleaved, wherein the peptide also contains a C-terminal detection moiety which can be released by a second peptidase only if the N-terminal methionine has been cleaved. Any cleaved peptide produced upon reaction with the composition is reacted with the second peptidase to release the detection moiety, which is then detected.

The second peptidase must be able to release the detection moiety from the peptide when the N-terminal methionine of the peptide has been removed. Additionally, the second peptidase must not be able to release the detection moiety from the peptide when an N-terminal Met is present. Also, since MAP can cleave the N-terminal Met from a peptide only when certain amino acids (e.g., Gly, Ala, Ser, Cys, Thr, Pro, or Val are present in the penultimate position of the peptide), the peptide-detection moiety which can be cleaved by the second peptidase must have one of those amino acids in the N-terminal position. Preferably, the second peptidase is dipeptidyl peptidase IV, which can utilize, e.g., Gly-Pr-p-nitroanilide as a substrate to release p-nitroanilide. Note that the N-terminal amino acid of this dipeptidyl peptidase IV substrate is Gly, which is a permissible penultimate amino acid for MAP. Thus, Met-Gly-Pro-p-nitroanilide can be cleaved by MAP to release Gly-Pro-p-nitroanilide, a dipeptidyl peptidase IV substrate, but Met-Gly-Pro-p-nitroanilide itself is not a dipeptidyl peptidase IV substrate. Therefore, dipeptidyl peptidase IV is a suitable second peptidase for this method. Other peptidases may also be useful as the second peptidase, for example triaminopeptidase, which can utilize Gly-Pro-Leu-detection moiety as a substrate (Aoyagi et al., 1978, *Biochem. Biophys. Res. Commun.* 80, 435), and cathepsin C, which can utilize Gly-Phe-detection moiety as a substrate (Jadot et al., 1984, *Biochem. J.,* 219, 965; Doughty and Gruenstein, 1986, *Biochem. and Cell Biol.,* 64, 772).

Preferably, the second peptidase is active under the same conditions as MAP (e.g., 10 mM Hepes, pH 7.35, 1.5 mM $MgCl_2$, 150 mM KCl, 10% glycerol, 0.1–0.5 mM $Co^{2+}$ [Buffer H], [Zuo et al., supra], 30–35° C.), to allow both peptidase reactions to occur without adjusting conditions. Such a second peptidase would allow the assay to be performed in one step, where the composition, peptide, and second peptidase are incubated simultaneously.

As previously discussed, the peptide to be used in the assay must have an N-terminal methionine which can be cleaved by MAP, i.e., it must have a penultimate amino acid which permits MAP to cleave the N-terminal methionine (e.g., Gly, Ala, Ser, Cys, Thr, Pro, or Val). The peptide must also have a C-terminal detection moiety which can be cleaved from the peptide by the second peptidase, only if the N-terminal methionine is not present. Thus, the sequence must permit such cleavage. When the second peptidase is dipeptidyl peptidase IV, permissible peptides include Met-$X_{aa1}$-$X_{aa2}$-detection moiety, where $X_{aa1}$ is Gly, Ala, Ser, Cys, Thr, Pro, or Val, preferably Ala, Cys, Gly, or Ser, most preferably Gly; and $X_{aa2}$ is Pro, Hyp, or Ala, most preferably Pro. Thus, the most preferred peptide for dipeptidyl peptidase IV is Met-Gly-Pro-detection moiety. However, any peptide which will result in release of the detection moiety when active MAP is present but not when MAP is absent can be useful in these methods. For example, multiples of the peptide cleavable by dipeptidyl peptidase IV may be used, for example Met-Gly-Pro-Gly-Pro-detection moiety, or Met-Gly-Pro-Gly-Pro-Gly-Pro-detection moiety, since dipeptidyl peptidase IV is capable of cleaving each successive dipeptide (after N-terminal Met cleavage by MAP) to release the detection moiety. The peptides of the present invention can be made by any method known in the art.

These methods can also employ a third enzyme which, in combination with MAP and the second peptidase (but not without MAP) releases or activates a detection moiety. In this scheme, the peptide is designed to accommodate the third enzyme. For example, the second peptidase and third enzyme can be dipeptidyl peptidase IV and cathepsin C, and the peptide can be Met-Gly-Pro-Gly-Phe-detection moiety or Met-Gly-Phe-Gly-Pro-detection moiety, where the second peptidase and the third enzyme work successively. Alternatively, the third enzyme can act on the detection moiety to produce a detectable signal. In that case, the detection moiety is a substrate for the third enzyme, for example luciferin for a luciferase third enzyme.

The invention is not narrowly limited by choice of detection moiety, provided the detection moiety is capable of being released from the peptide to produce a detectable signal. The detection moiety can be a moiety which can be determined by a secondary step, for example by a chromatographic, centrifugal, or electrophoretic separation, or by enzyme reaction (as previously discussed). In this regard, the detection moiety can itself be an enzyme, provided that (1) the enzyme has increased activity when released from the peptide by the second peptidase, and (2) the enzyme has activity for a substrate which can be detected after the enzyme acts on it. Preferably, the detection moiety is one that can be easily detected, for example by visual, photometric, spectrometric, or fluorescent means. Non-limiting examples of such moieties are cresyl violet, which is fluorescent when released (Van Noorden et al., 1997, *Anal. Biochem.* 252, 71–77); 7-amino-3-trifluoromethylcoumarine, also fluorescent when released (Lojda, 1996, *Acta Histochem* 98, 215–218); 4-methoxy-2-naphthylamine (Scharpe et al., 1988, *Clin. Chem.* 34, 2299–2301) or 2-naphthylamine (Ikehara et al., supra), which are also fluorescent upon release; 1-hydroxy-4-naphthylamide, which, when released, react with tetrazolium salts to form a water-insoluble, deeply colored formazans (useful for certain solid phase formats of the method); 3,5-dibromo-4-hydroxyanilide, which forms 2,6-dibromophenol-indo-p-xylenol upon release, a compound with an absorption maxima at 600 nm (Shibuya-Saruta et al., 1995, *J. Clin. Lab. Anal.* 9, 113–118); and p-nitroanilide, which has an absorption maxima at 415 nm when released (Id.). A preferred detection moiety is p-nitroanilide, because it has been widely used, e.g., as a detection moiety in dipeptidyl peptidase assays (using, e.g., the peptide Gly-Pro-p-nitroanilide). Several different detection methods have been used to detect p-nitroanilide (Ikehara, supra). For example, this compound can be visualized, or measured directly photometrically or spectrometrically at, e.g., 385 nm. A more sensitive p-nitroanilide detection method involves diazotization and coupling with N-(1-naphthyl) ethylenediamine to produce a product which can be measured at 548 nm (Id).

The invention encompasses various assay formats. For example, the assay can be performed in a two-step method, by first mixing the composition (where MAP may be present) with the peptide, allowing any MAP present to cleave the N-terminal methionine from the peptide, then adding the second peptidase, allowing the detection moiety to be released. This format may be useful where the second peptidase has different requirements for activity (e.g., different pH or temperature optima), where the conditions can be changed prior to adding the second peptidase. Preferably, however, the assay is performed in one step, where the composition, the peptide, and the second peptidase are mixed together and incubated to allow the detection moiety to be released.

The methods can also be performed wholly in an aqueous solution (e.g., in tubes or microtiter wells), or partly or wholly on a solid phase. The solid phase can be employed, e.g., where a peptidase is adsorbed or covalently bound to a bead, tube, or well and the other components are in solution, or where the entire assay is performed on a solid phase such as a nitrocellulose membrane, and the detection moiety produces an insoluble detectable product upon release from the peptide. Such a solid phase format can also be used in histochemical applications to localize MAP present in tissue. In those applications, the peptide along with the dipeptidyl peptidase IV is applied to the tissue. Preferably, the detection moiety will be insoluble when released from the peptide, to prevent the MAP "signal" from moving from the MAP location in the tissue.

These methods can be used qualitatively or quantitatively. For example, the methods can be used qualitatively to monitor production or purification of MAP by simply visualizing the released detection moiety. The method can also be used to quantitatively monitor such production or purification, or measure MAP activity, e.g., in tissue or fluid samples, by quantifying the detection moiety, and comparing the value with controls of known MAP activity.

In other embodiments of the invention, methods are provided for determining whether a substance inhibits a MAP. These methods are performed like the method for MAP activity disclosed above, except that a constant amount of MAP is utilized, and the substance is added before the MAP is combined with the peptide. Thus, the method comprises combining the substance, the MAP, and a peptide comprising an N-terminal methionine under conditions that the N-terminal methionine can be cleaved from the peptide by the MAP to produce a cleaved peptide, wherein the peptide contains a C-terminal detection moiety which is released by a second peptidase only if the N-terminal methionine has been cleaved from the peptide; reacting any cleaved peptide produced with the second peptidase to release the detection moiety; and detecting any detection moiety released. If the substance inhibits MAP, there will be less (or no) detection moiety released from the peptide than if the substance does not inhibit MAP. Thus, it is preferred that a no-inhibitor control is utilized in order to be able to determine if the detection moiety released is less than that released without the inhibitor. It is also preferred that a control be utilized to rule out inhibition of the second peptidase, rather than the MAP. For example, where the second peptidase is dipeptidyl peptidase IV, such a control would be the use of the peptide Gly-Pro-p-nitroanilide instead of Met-Gly-Pro-p-nitroanilide.

This inhibitor-detection method can utilize MAP or the second peptidase from any source. However, since some known inhibitors of MAP only inhibit some forms of MAP (e.g., fumagillin inhibits type 2, but not type 1, MAP), the MAP selected for this assay should be similar or the same as the MAP to which inhibition is desired.

The MAP and second peptidase can be in purified form or in an impure form, such as a cell lysate, provided the other components of the impure preparation do not interfere with the MAP-peptide or MAP-second peptidase reaction. In one variation, the MAP and second peptidase can be produced in transgenic cells (prepared by methods known in the art) to which the peptide and inhibitor are added.

These methods can be used to qualitatively or quantitatively screen for MAP inhibitors. For example, the methods can be used qualitatively to evaluate whether a substance is a strong MAP inhibitor, where the difference in released detection moiety between treatments with a sought-after inhibitor and treatments or controls without such an inhibitor can be readily ascertained visually. The methods can also be used to quantitatively evaluate the relative inhibitory activity of a substance, or quantify the amount of an inhibitor in, e.g., tissue or fluid samples, by quantifying the released detection moiety and comparing the value with controls having known amounts of an inhibitor. For example, the amount of fumigillin in the tissue of a cancer patient treated with that MAP inhibitor to prevent angiogenesis can be monitored with these methods.

These inhibitor-detecting methods can also be utilized to simultaneously screen compounds for inhibitor activity of MAP and the second peptidase, and/or the third enzyme, if so employed. In this scheme, the inhibitor is added with MAP, the second peptidase, and the third enzyme, if desired. Any substance inhibiting release of the detection moiety is then evaluated for inhibition of the second peptidase and/or the third enzyme. For example, MAP, dipeptidyl peptidase IV, cathepsin C, and the peptide Met-Gly-Pro-Gly-Phe-p-nitroanilide can be used to test for inhibitory activity of a substance. If the substance is not inhibitory to any of these enzymes, p-nitroanilide will be released. However, if a reduced amount of p-nitroanilide is released, the substance can then be tested using Gly-Pro-p-nitroanilide (a dipeptidyl peptidase IV substrate) or Gly-Phe-p-nitroanilide (a cathepsin C substrate). If the inhibitor does not inhibit release of p-nitroanilide in either of these tests, then the inhibitor is specific for MAP. If the inhibitor does not allow the release of p-nitroanilide when Gly-Prop-nitroanilide was used, but does allow release when Gly-Phe-p-nitroanilide was used, the inhibitor is specific for dipeptidyl peptidase IV; if the result is the opposite, then the inhibitor is specific for cathepsin C.

In additional embodiments of the invention, reaction mixtures are provided which are useful for either the method for detecting MAP, or the method for detecting an inhibitor of MAP, the second peptidase, or the third enzyme. The reaction mixtures comprise a mixture of (a) a peptide comprising an N-terminal methionine which can be cleaved by the MAP, and a C-terminal detection moiety which can be released by a second peptidase only if the N-terminal methionine has been cleaved from the peptide, and (b) the second peptidase. Additionally, the reaction mixtures of this embodiment must be suitable for use as the reaction mixture of the method for detecting MAP described above in that factors such as pH and ionic strength must be suitable for activity of the MAP and second peptidase. A preferred second peptidase in this reaction mixture is dipeptidyl peptidase IV. When the second peptidase is dipeptidyl peptidase IV, a preferred peptide comprises Met-$X_{aa}$-Pro, wherein $X_{aa}$ is Ala, Cys, Gly, or Ser, and the most preferred peptide is Met-Gly-Pro-p-nitroanilide. These reaction mixtures may also comprise a MAP, which is useful for the methods for detecting MAP inhibitors.

In still other embodiments of the invention, kits are provided which are useful for performing the method for detecting MAP, or the method for detecting an inhibitor of MAP, the second peptidase, or the third enzyme. The kits comprise (a) a peptide comprising an N-terminal methionine which can be cleaved by the MAP, and a C-terminal detection moiety which can be released by a second peptidase only if the N-terminal methionine has been cleaved from the peptide, (b) the second peptidase, and (c) instructions for performing the method. A preferred second peptidase in these kits are dipeptidyl peptidase IV. When the second peptidase is dipeptidyl peptidase IV, a preferred peptide comprises Met-$X_{aa}$-Pro, wherein $X_{aa}$ is Ala, Cys, Gly, or Ser, and the most preferred peptide is Met-Gly-Pro-p-nitroanilide. These kits preferably also comprise a MAP, which is useful for the methods for detecting MAP inhibitors, or as a component of a control in methods for detecting MAP. The components of these kits can be in separate containers, or some or all of the components may be mixed together.

In additional embodiments of the invention, peptides are provided which comprise an N-terminal methionine which can be cleaved by a methionine aminopeptidase, and a C-terminal detection moiety which can be released by a second peptidase only if the N-terminal methionine has been cleaved from the peptide. A preferred peptide for these embodiments comprises Met-$X_{aa}$-Pro, wherein $X_{aa}$ is Ala, Cys, Gly, or Ser, and the most preferred peptide is Met-Gly-Pro-p-nitroanilide.

INDUSTRIAL APPLICATION

The methods and compositions of the present invention are useful for detecting MAP or MAP inhibitors rapidly and quantitatively, for isolating, purifying, or quantifying new MAPs or inhibitors of MAPs, or for determining or quantifying MAP activity in a sample.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE

This example illustrates embodiments of the method for quantifying MAP and the method for detecting an inhibitor of MAP according to the invention.

To determine whether Met-Gly-Pro-p-nitroanilide is a substrate for MAP, and whether the presence of dipeptidyl peptidase could affect the activity of MAP, an AccQ-Tag assay was used as described in Zuo et al., supra. Table 1 shows that this peptide is a substrate for both type 1 and type 2 MAP.

TABLE 1

Kinetic parameters for yeast type 1 MAP and human type 2 MAP.
Data are reported as mean ± SD.

| Enzymes    | $k_{cat}$ (min$^{-1}$) | $K_m$ (mM) | $k_{cat}/K_m$ (mM$^{-1}$min$^{-1}$) |
|------------|------------------------|-------------|--------------------------------------|
| type 1 MAP | 864 ± 25               | 4 ± 0.7     | 216 ± 35                             |
| type 2 MAP | 518 ± 35               | 3 ± 0.5     | 172 ± 26                             |

The activity of both type 1 MAP and type 2 MAP was not affected by the addition of dipeptidyl peptidase IV.

MAP activity was next determined by monitoring the release of p-nitroanilide in a microtiter format. Purified type 1 MAP or type 2 MAP (0.6 μg) and/or 0.001 unit of dipeptidyl peptidase IV was added in 47 μl of buffer H (10 mM Hepes, pH 7.4, 10% glycerol), containing 0.1 M KCl and 0.1 mM of Co$^{2+}$ in wells of a 96-well microtiter plate. After incubating at 37° C. for 5 min, 2 mM of Met-Gly-Pro-p-nitroanilide was added to the mixture to start the reaction. A microtiter plate reader, set at 405 nm to detect released p-nitroanilide, was used to record the progress of the reactions. As shown in FIG. 2, significant increases in released p-nitroanilide occurred only when MAP (either type) is present along with dipeptidyl peptidase IV. These curves are highly reproducible and linear, with correlation coefficients ($r^2$)>0.98.

Figure 3:
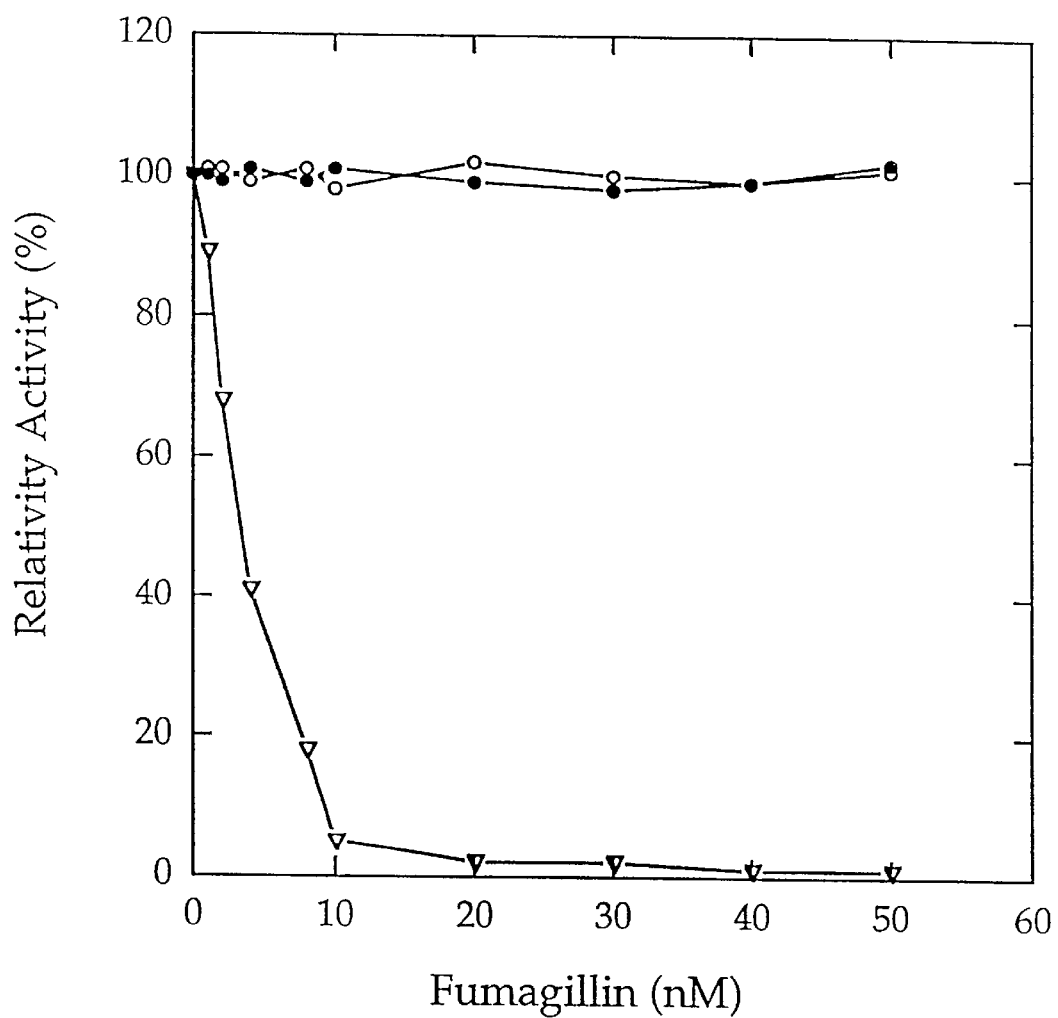
FIG. 3 is a graph depicting the results of an assay for inhibition of MAP by fumagillin according to the present invention, using dipeptidyl peptidase IV and the peptide Met-Gly-Pro-p-nitroanilide, where fumagillin strongly inhibited release of p-nitroanilide when type 2 MAP was used (∇—∇), but not when type 1 MAP was used (o—o), or when dipeptidyl peptidase IV was used with Gly-Pro-p-nitroanilide (•—•).

To demonstrate the use of this method in detecting a type 2 MAP inhibitor, various amounts of fumigillin were added to each reaction. After incubating the inhibitor with MAP solutions at 37° C. for 10 min, 2 mM of Met-Gly-Pro-p-nitroanilide was added to start the reaction, and the release of p-nitroanilide was monitored with a microtiter plate reader at 405 nm as described above. The effect of fumigillin on dipeptidyl peptidase IV activity was also tested by using Gly-Pro-p-nitroanilide as the substrate. As shown in FIG. 3, while both type 1 MAP and dipeptidyl peptidase IV activity remained unaffected even in the presence of 50 nM fumagillin, type 2 MAP activity was completely inhibited by 20 nM fumigillin. These results are very similar to those obtained with the AccQ-Tag method (Griffith et al., supra), indicating that this is a reliable method for identifying new MAP inhibitors.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for detecting methionine aminopeptidase (MAP) activity in a composition comprising:
    (a) combining the composition with a peptide comprising an N-terminal methionine under conditions that the N-terminal methionine can be cleaved from the peptide by a MAP to produce a cleaved peptide, wherein the peptide contains a C-terminal detection moiety which is released by a second peptidase only if the N-terminal methionine has been cleaved from the peptide;
    (b) reacting any cleaved peptide produced in (a) with the second peptidase to release the detection moiety;
    (c) detecting any detection moiety released
    (d) correlating any detected moiety released with detecting MAP activity.

2. The method of claim 1, wherein (a) and (b) are performed in one aqueous reaction mixture.

3. The method of claim 1, wherein the detection moiety is p-nitroanilide.

4. The method of claim 1, wherein the second peptidase is dipeptidyl peptidase IV and the peptide comprises Met-$X_{aa}$-Pro, wherein $X_{aa}$ is Ala, Cys, Gly, or Ser.

5. The method of claim 4, wherein the peptide is Met-Gly-Pro-p-nitroanilide.

6. The method of claim 1, wherein the MAP is a type 2 MAP.

7. The method of claim 6, wherein the MAP is a human MAP.

8. A method for determining whether a substance inhibits a methionine aminopeptidase (MAP) comprising:
    (a) combining the substance, the MAP, and a peptide comprising an N-terminal methionine under conditions that the N-terminal methionine can be cleaved from the peptide by the MAP to produce a cleaved peptide, wherein the peptide contains a C-terminal detection moiety which is released by a second peptidase only if the N-terminal methionine has been cleaved from the peptide;
    (b) reacting any cleaved peptide produced in (a) with the second peptidase to release the detection moiety;
    (c) detecting any detection moiety released
    (d) correlating any detected moiety released with determining whether a substance inhibits MAP activity.

9. The method of claim 8, wherein the detecting step comprises quantitating the amount of detection moiety released.

10. The method of claim 8, wherein (a) and (b) are both performed in one aqueous reaction mixture.

11. The method of claim 8, wherein the second peptidase is dipeptidyl peptidase IV and the peptide comprises Met-$X_{aa}$-Pro, wherein $X_{aa}$ is Ala, Cys, Gly, or Ser.

12. The method of claim 8, wherein the C-terminal detection moiety comprises p-nitroanilide.

13. The method of claim 8, wherein the peptide is Met-Gly-Pro-p-nitroanilide.

* * * * *